United States Patent
Drasler et al.

(10) Patent No.: US 8,814,859 B2
(45) Date of Patent: Aug. 26, 2014

(54) VASCULAR SEALING DEVICE AND METHOD USING CLOT ENHANCING BALLOON AND ELECTRIC FIELD GENERATION

(71) Applicant: Boston Scientific Scimed, Inc., Maple Grove, MN (US)

(72) Inventors: William J. Drasler, Minnetonka, MN (US); Tracee Eidenschink, Wayzata, MN (US); Joseph M. Thielen, Buffalo, MN (US); Mark L. Jenson, Greenfield, MN (US); Anu Sadisiva, Maple Grove, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 13/775,136

(22) Filed: Feb. 23, 2013

(65) Prior Publication Data

US 2013/0172886 A1 Jul. 4, 2013

Related U.S. Application Data

(63) Continuation of application No. 12/026,067, filed on Feb. 5, 2008, now abandoned.

(60) Provisional application No. 60/888,202, filed on Feb. 5, 2007.

(51) Int. Cl.
*A61B 18/14* (2006.01)

(52) U.S. Cl.
USPC .......................................................... 606/41

(58) Field of Classification Search
USPC .................................. 606/27, 30–32, 40, 41
See application file for complete search history.

(56) References Cited

U.S. PATENT DOCUMENTS

| | | | |
|---|---|---|---|
| 4,315,512 A * | 2/1982 | Fogarty | 606/194 |
| 4,709,698 A | 12/1987 | Johnston et al. | |
| 5,415,657 A | 5/1995 | Taymor-Luria | |
| 5,507,744 A | 4/1996 | Tay et al. | |
| 5,725,551 A | 3/1998 | Myers et al. | |

(Continued)

FOREIGN PATENT DOCUMENTS

WO 2008033628 A1 3/2008

*Primary Examiner* — Michael Peffley
*Assistant Examiner* — Daniel Fowler
(74) *Attorney, Agent, or Firm* — Seager, Tufte & Wickhem LLC (57) ABSTRACT

An apparatus and method for closing an opening in a blood vessel wall is disclosed. The apparatus includes at least one member which is extended through a tissue tract formed through the epidermis and subcutaneous layer of skin and through the opening in the blood vessel. The member includes a proximal end and a distal end with the distal end being positionable proximate to the opening in the blood vessel wall. A positive electrode is positioned next to the distal end with a negative electrode being positioned next to the proximal end When the electrodes are energized an electric field is created therebetween, blood cells are attracted to the positive electrode, and a thrombus is formed at the opening in the blood vessel wall. The member may include a balloon at the distal end to temporarily occlude blood flow from the blood vessel to the tissue tract to facilitate formation of the thrombus. In addition, the shape of the balloon may be tailored to facilitate the formation of the thrombus including, but not limited to, the creation of pockets and self-supporting balloons.

6 Claims, 10 Drawing Sheets

(56) References Cited

U.S. PATENT DOCUMENTS

| | | |
|---|---|---|
| 5,797,947 A | 8/1998 | Mollenauer |
| 5,810,810 A | 9/1998 | Tay et al. |
| 6,019,757 A | 2/2000 | Scheldrup |
| 6,048,357 A | 4/2000 | Kontos |
| 6,302,898 B1 | 10/2001 | Edwards et al. |
| 6,325,818 B1 | 12/2001 | Werneth |
| 6,398,782 B1 | 6/2002 | Pecor et al. |
| 7,223,266 B2 | 5/2007 | Lindenbaum et al. |
| 7,458,974 B1 | 12/2008 | Hayashi et al. |
| 7,790,192 B2 | 9/2010 | Khosravi et al. |
| 7,806,856 B2 | 10/2010 | Bagaoisan et al. |
| 2003/0109866 A1 | 6/2003 | Edwards et al. |
| 2004/0153060 A1 | 8/2004 | Lindenbaum et al. |
| 2004/0215233 A1* | 10/2004 | Kaplan et al. ......... 606/213 |
| 2006/0034930 A1 | 2/2006 | Khosravi et al. |

* cited by examiner

FIG. 15

VASCULAR SEALING DEVICE AND METHOD USING CLOT ENHANCING BALLOON AND ELECTRIC FIELD GENERATION

CROSS-REFERENCE TO RELATED APPLICATION

This application is a continuation of U.S. application Ser. No. 12/026,067 filed on Feb. 5, 2008, which is a non-provisional patent application claiming priority under 35 USC .sctn. 119(e) to U.S. provisional patent application Ser. No. 60/888,202 filed on Feb. 5, 2007.

FIELD OF THE DISCLOSURE

The present disclosure generally relates to medical devices and, more particularly, relates to apparatus and methods for closing openings in blood vessels.

BACKGROUND OF THE DISCLOSURE

In many medical procedures, such as balloon angioplasty and the like, it is known how to create an opening in a blood vessel, known as an arteriotomy, to allow for the insertion of various medical devices which can be navigated through the blood vessel to the site to be treated. Typically, the opening is formed in the femoral artery at a point proximate the groin and a series of medical devices are inserted in sequence. For example, a guide wire may first be inserted through the tissue tract created between the skin or the epidermis of the patient down through the subcutaneous tissue and into the opening formed in the blood vessel The guide wire is then navigated through the blood vessel to the site of the occlusion, the heart, or any other area to be treated. Once the guide wire is in place, a working sheath can be slid over the guide wire to form a wider, more easily accessible, tract between the epidermis and the opening into the blood vessel If an angioplasty needs to be performed, the balloon catheter can then be introduced over the guide wire again through the working sheath, through the opening in the femoral artery, and then up to the blood vessel to the site of the occlusion.

Once the procedure is performed, the guide wire, balloon catheter and any other equipment introduced can be retracted through the blood vessel, out through the opening in the blood vessel wall, out through the working sheath, and out of the body entirely. The working sheath can then be removed whereby the physician or other medical technician is presented with the challenge of trying to close the opening both in the femoral artery and the tissue tract formed in the epidermis and subcutaneous tissue Most importantly, the opening in the blood vessel must be closed as soon as possible.

Over the years that these procedures have been performed, a number of apparatus and methods have been created fbi closing the opening in the blood vessel. Traditionally, and still commonly today, the opening is closed simply by the application of manual pressure If sufficient pressure is applied, the blood vessel is constricted until a clot or thrombus forms whereupon the pressure can be removed and eventually the patient can become ambulatory once again However, a number of drawbacks are associated with such a method For one, the process is very time consuming often taking many hours fbi the thrombus to fully form, during which time the patient is required to be stationary. In addition, the mere application of such significant pressure to the groin is often quite uncomfortable for the patient.

In light of these difficulties, a number of proposals have been introduced to potentially alleviate such drawbacks. In one approach, an anchor is inserted through the tissue tract and the blood vessel with a filament extending therefrom and connected to a sealing plug by a pulley arrangement. Once the anchor engages an interior surface of the blood vessel the filament can be used to pull the sealing plug securely into the tissue tract. While this approach does more quickly close the opening in the blood vessel than manual pressure application, it also results in the unfavorable characteristic of leaving a foreign body in the patient after the procedure is completed.

Another approach uses a resistive heating coil inserted into the opening in the blood vessel. Upon energization of the heating coil, the blood in the vicinity of the opening is caused to coagulate given the rise in temperature. This can be accomplished in combination with the introduction of a procoagulant into the site to again expedite the creation of the coagulation While this approach has also met with some level of success, it also results in the introduction of a foreign body and/or substance into the tissue of the patient.

A still further approach involves the introduction of a collagen plug into the site of the opening. Such a plug is sized to be frictionally engaged by the sides of the opening in the blood vessel and thus held in place until coagulation of blood forms around the collagen plug. The collagen plug is biodegradable and eventually is dispersed into the blood flow and eliminated from the body. However, just the introduction of such a foreign substance into the body can sometimes be, at the very least, inflammatory and uncomfortable for the patient In one collagen plug approach, a balloon catheter is inserted into the blood vessel, inflated, and then pulled back against an interior surface of the blood vessel wall to serve as a backstop. The collagen plug in such an approach is shaped and sized as to closely match the opening in the blood vessel wall and is pushed down into the tissue tract until it engages the inflated balloon. The inflated balloon can then be deflated and withdrawn leaving the collagen plug in place.

In another collagen plug approach, a delivery sheath wider than the opening in the blood vessel wall is used and then a collagen plug corresponding to the size of the inner diameter of the delivery sheath is pushed through the sheath so as to engage the outer surface of the blood vessel wall The plug can then be tamped or compressed down against the exterior surface of the blood vessel wall such that a portion of the collagen extends into the opening of the blood vessel wall While each of the foregoing approaches have been met with some level of success, it can be seen that each also has substantial drawbacks. Accordingly, it would be advantageous for the art to provide an apparatus and method which can quickly close the opening in the blood vessel wall, minimizes any decrease in blood flow through the blood vessel during the closure procedure, forms a thrombus which reliably remains in place after formation, minimizes patient discomfort, introduces no foreign body or substance into the blood vessel and leaves no foreign bodies behind after the procedure is completed.

SUMMARY OF THE DISCLOSURE

According to one aspect of the disclosure, an apparatus is disclosed for closing an opening in a blood vessel. The apparatus may include a sheath extending from the epidermis of a patient to a blood vessel, the sheath having a proximal end positionable at the epidermis of the patient and a distal end positionable at the blood vessel wall of the patient. The apparatus further includes a balloon catheter inserted through the sheath with the balloon catheter having a proximal end positionable at the epidermis of the patient and a distal end positionable within the blood vessel of the patient. The apparatus further includes first and second electrodes with the first electrode being at the proximal end of the sheath and balloon catheter, and the second electrode being at the distal end of the balloon catheter.

In accordance with another aspect of the disclosure, an apparatus for closing an opening in a blood vessel is disclosed which comprises a member for extending between an epidermis of a patient and a blood vessel wall of a patient, a first electrode, and a second electrode. The member includes a proximal end positionable at the epidermis and distal end positionable at the blood vessel wall with the first electrode being at the member proximal end and the second electrode being at the member distal end.

In accordance with another aspect of the disclosure, a method of closing an opening in a blood vessel is disclosed comprising inserting a sheath into a tissue tract of a patient extending between an epidermis and a blood vessel wall, extending a balloon catheter into the sheath, the balloon catheter having a shaft extending into a balloon, the balloon catheter being inserted until the balloon is entirely within the blood vessel, at least one of the sheath and balloon catheter having a positive electrode thereon, at least one of the sheath and balloon catheter having a negative electrode thereon, inflating the balloon, retracting the balloon until the inflated balloon engages an interior surface of the blood vessel wall, and creating an electric field between the negative and positive electrodes, cells thereby being attracted to the positive electrode and forming a thrombus at the blood vessel wall.

In accordance with another aspect of the disclosure, a method of closing an opening in a blood vessel is disclosed which comprises inserting a member between the epidermis of the patient and the opening of the blood vessel wall of the patient, the member having a positive electrode and negative electrode thereon, and creating a electric field between the negative and positive electrodes, cells thereby being attracted to the positive electrode and forming a thrombus at the blood vessel wall. The member includes proximal and distal ends with the distal end being positionable at the blood vessel wall, and the positive electrode being provided at the member distal end These and other aspects and features of the disclosure will become mole apparent upon reading the following detailed description when taken in conjunction with the accompanying drawings.

While the present disclosure is susceptible to various modifications and alternatives constructions, certain illustrative embodiments have been shown in the drawings and will be described below in detail. It should be understood, however, that there is no intention to limit the present invention to the specific forms disclosed, but on the contrary, the intention is to cover all modifications, alternative constructions, and equivalents falling within the spirit and scope of the present invention.

DETAILED DESCRIPTION OF THE DISCLOSURE

Figure 1:
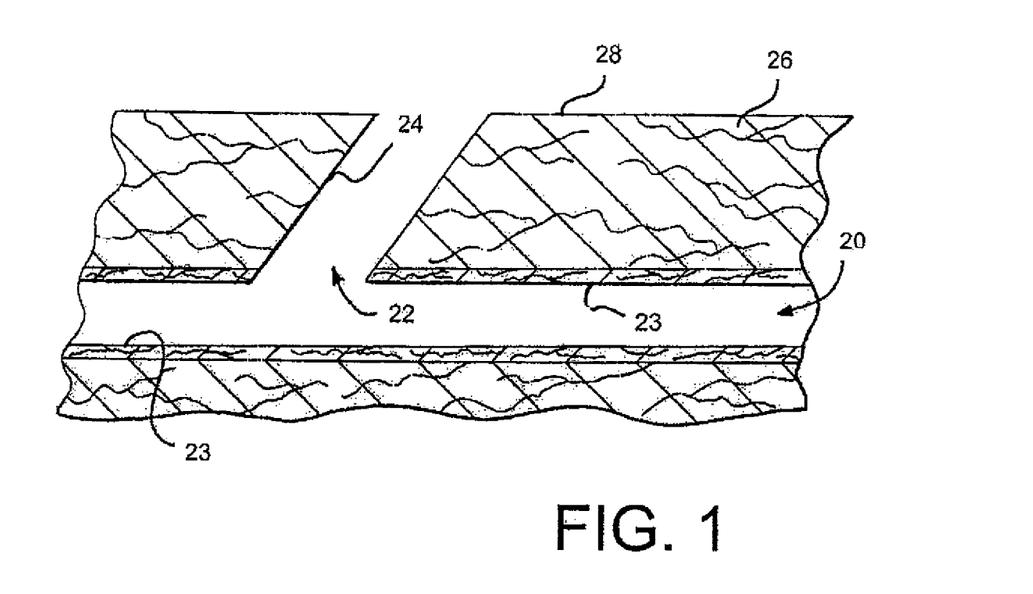
FIG. 1 is a cross-sectional view of a blood vessel, subcutaneous layer, and epidermis layer with a tissue tract formed between the epidermis, through the subcutaneous layer, and to the blood vessel wall.

Referring now to the drawings and with specific reference to FIG. 1, a blood vessel 20 is depicted with an opening 22 therein after the completion of a medical procedure such as, but not limited to, a balloon angioplasty. As stated above with respect to the background, in such a procedure, an opening or arteriotomy 22 is provided in a wall 23 of the blood vessel 20 to allow access into and passage through the blood vessel of the various medical devices needed for the medical procedure. After such medical devices are used and removed from the opening and through a tissue tract 24 extending between a blood vessel 20 and a subcutaneous layer 26, and an epidermis layer 28, the opening 22 and tract 24 need to be closed. The pending disclosure is primarily directed to an apparatus and method for closing the opening 22 in the blood vessel wall 23.

Figure 2:
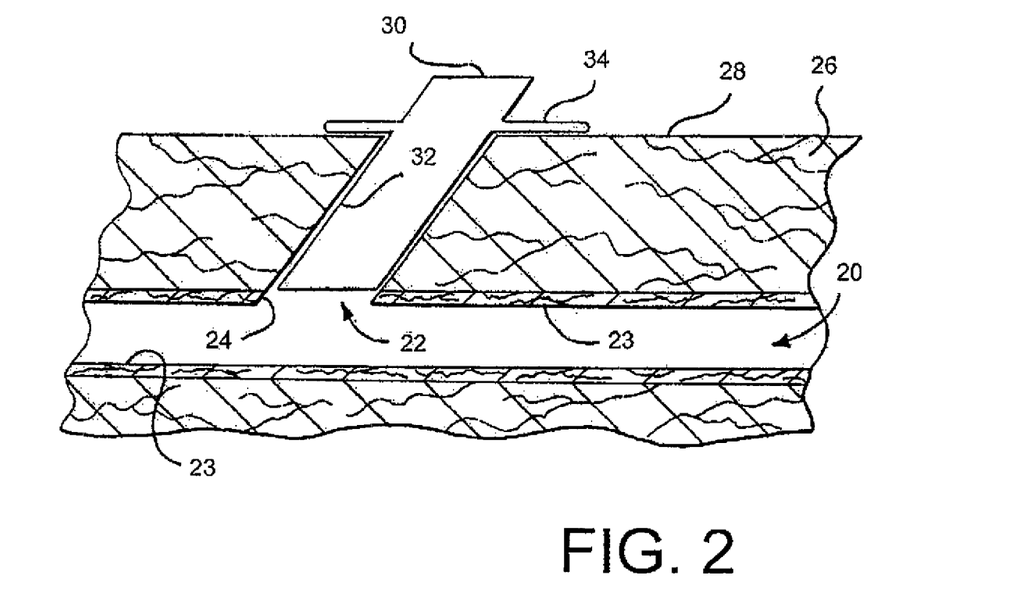
FIG. 2 is a sectional view similar to FIG. 1, but with a working sheath/sleeve extended through the tissue tract.

Referring now to FIG. 2, a first step according to the present disclosure is to insert a working sheath 30 into the tissue tract 24 substantially to the opening 22 in the blood vessel wall 23. The working sheath 30 may include a main cylindrical body 32. A circumferential flange 34 can be movably located around the sheath 30 to provide a flange electrode located on the skin. Other electrode designs can also be used to allow for current flow. The working sheath 30 may be provided in any number of different forms and may or may not include the flange 34 or could be provided with other indicia on the main body 32 informing the physician or other medical technician the distance the working sheath should be introduced into the tract 24. In addition, the working sheath 30 may be slid along a guide wire (not shown) and extended through the tract 24 and into the blood vessel 20. However, for the purpose of illustration, and ease of understanding, the guide wire is not depicted.

Figure 3:
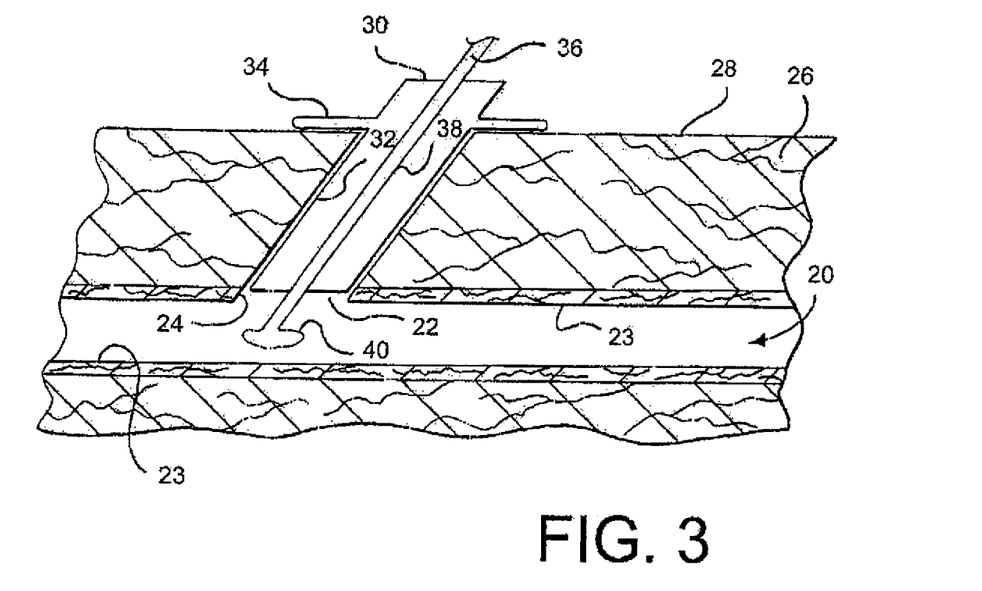
FIG. 3 is a view similar to FIG. 2, but with an uninflated balloon catheter being extended through the introducer sheath.

Referring now to FIG. 3, a next step is depicted where a balloon catheter 36 is extended into the working sheath 30. The balloon catheter includes a shaft 38 from which a balloon 40 extends The balloon catheter 36 is extended through the working sheath 30 in an uninflated state. The balloon catheter 36 is extended to a distance necessary to allow the balloon 40 to be fully received within the blood vessel 20. Alternatively, the apparatus could work in conjunction with a conventional introducer sheath wherein the balloon catheter is slid through an introducer sheath and the working sheath is then slid through the introducer sheath In such an embodiment, the negative electrode mentioned later herein could be located in the working sheath.

Figure 4:
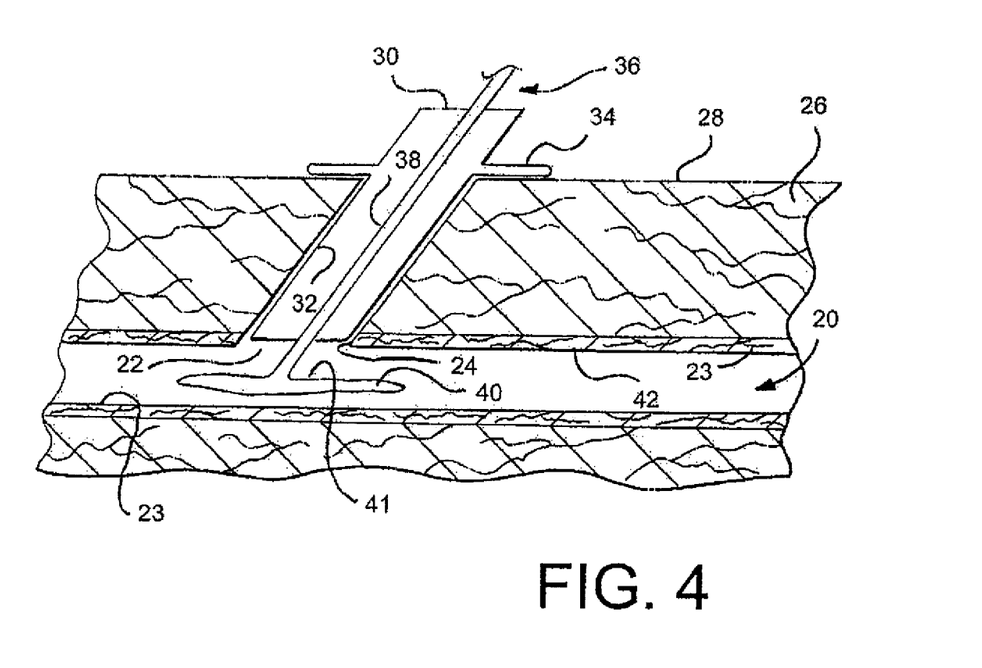
FIG. 4 is a view similar to FIG. 3, but with the balloon catheter inflated.

Referring now to FIG. 4, it is seen that the balloon 40 is then inflated, i.e., by the introduction of air or fluid into the balloon shaft and ultimately the interior of the balloon 40. The balloon 40 is of such a size that even when inflated, blood flow through the blood vessel 20 is not fully occluded, but does allow for a certain degree of perfusion therethrough. After the balloon 40 is fully inflated, the balloon catheter 36 is retracted away from the center of the blood vessel 20 such that an upper surface 41 of a balloon 40 engages an inner surface 42 of the blood vessel wall 23 In so doing, it will be readily understood by one of ordinary skill in the art that the opening 22 is substantially sealed preventing any significant level of blood flow between the blood vessel 20 and the tissue tract 24.

Figure 5:
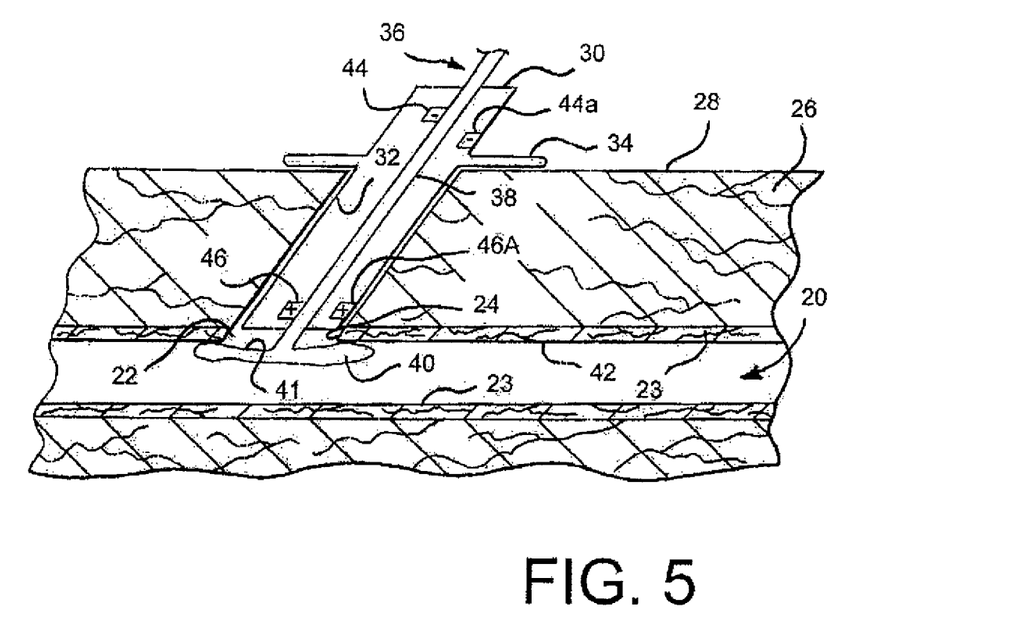
FIG. 5 is a view similar to FIG. 4, but with the balloon catheter inflated and retracted to be against the inner surface of the blood vessel wall.
Figure 6:
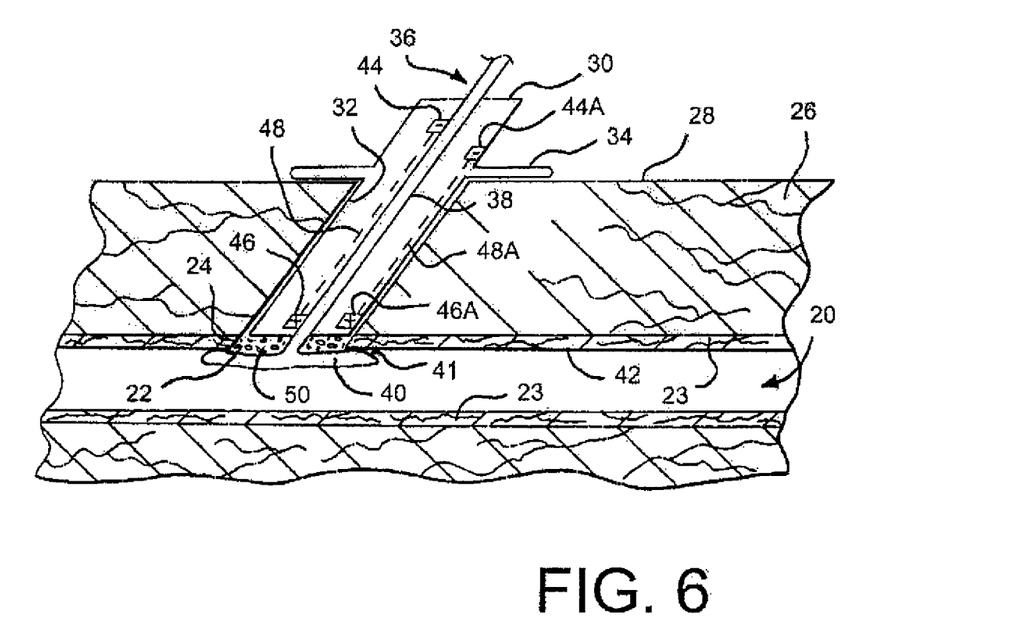
FIG. 6 is a view similar to FIG. 5, but with electrodes creating an electric field and thereby drawing cells to the positive electrode.
Figure 7:
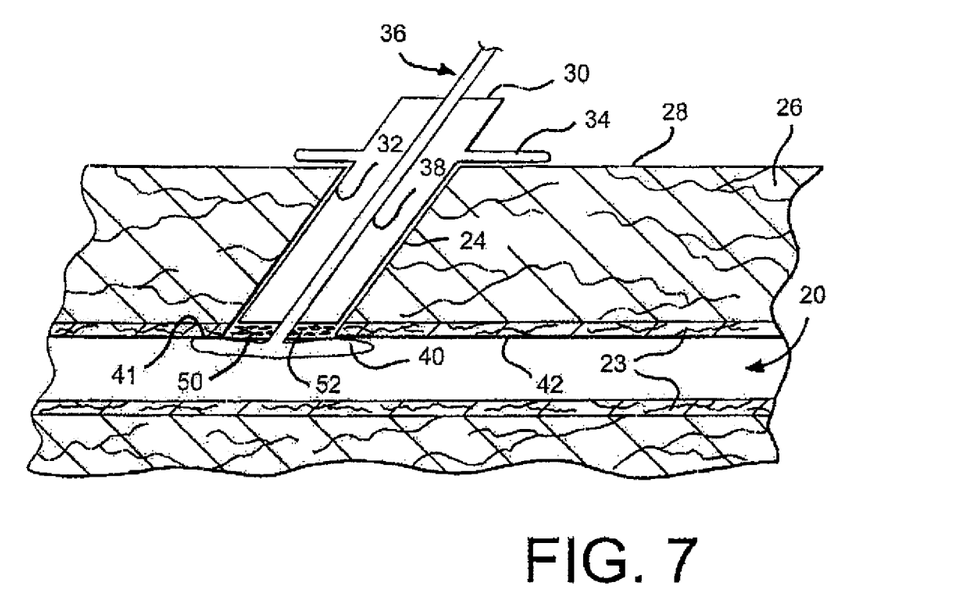
FIG. 7 is a view similar to FIG. 6, after a thrombus has formed and prior to the balloon catheter and working sheath being retracted.
Figure 8:
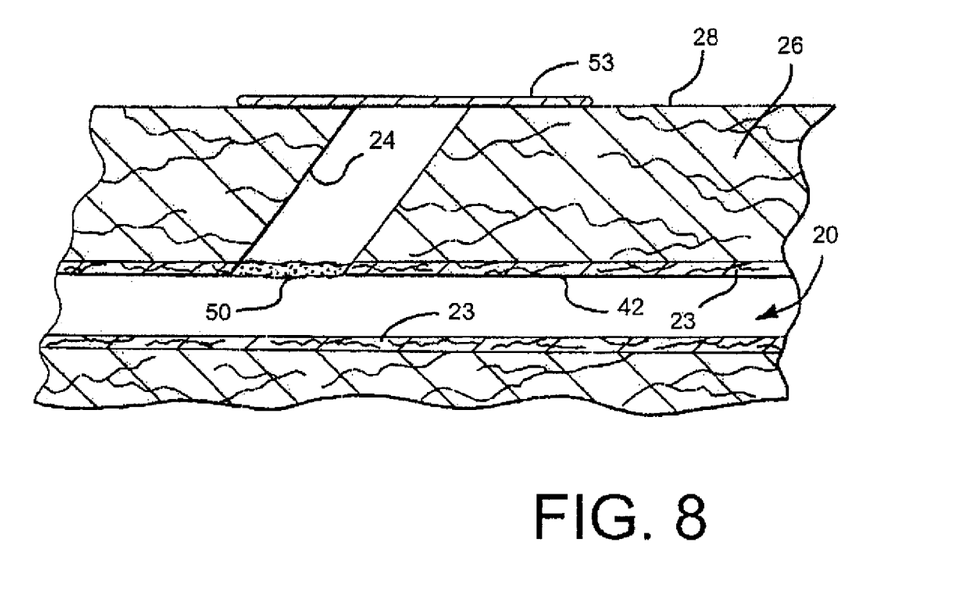
FIG. 8 is a view similar to FIG. 7, but with the thrombus fully formed after the balloon catheter and working sheath are withdrawn.

Once the physician reaches the position depicted in FIG. 5, as determined based on the degree of resistance felt when retracting the balloon 40 and lack of blood flow out of the tissue t act 24, the physician or other medical technician can energize first electrode 44 and second electrode 46. In so doing, an electric field 48 is created between the first and second electrodes 44 and 46 as shown in FIG. 6. In addition to the layout of FIG. 6, additional electrode configurations are available within the scope of this disclosure to create multiple fields and further aid in thrombus formation By positioning the electrodes appropriately, the blood cells within the tissue tract 24 are attracted to a position where it is desired to have a thrombus 50 formed More specifically, the platelets of the blood are attracted to the positive electrode, even in blood which has been treated with a blood thinner or other anticoagulant, such as heparin Since such blood cells are attracted to a positive electrode, by positioning the positive electrode appropriately, a thrombus can be formed in a desired location Thus in the depicted embodiments, the first electrode 44 is negatively charged and the second electrode 46 is positively charged, with the second electrode being provided at a position proximate the blood vessel wall 23 The thrombus 50 is therefore formed as shown in FIGS. 6, 7, and 8 at the juncture between the blood vessel wall 23 and the tissue tract 24 Alternatively, the positively charged electrode can be located along the shaft of the balloon catheter, at the distal end of the shaft, or on a portion of the balloon. By the same token, the negative electrode can be located on the skin of the patient.

Figure 12A:
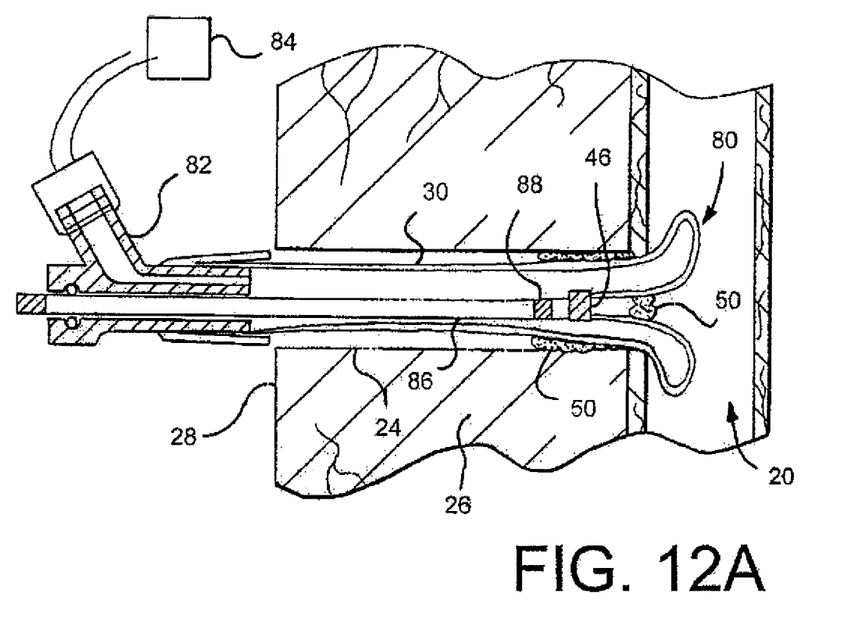
FIG. 12*a* is a sectional view of an alternative embodiment using a rolling membrane balloon and depicted in an un-deployed configuration.
Figure 12B:
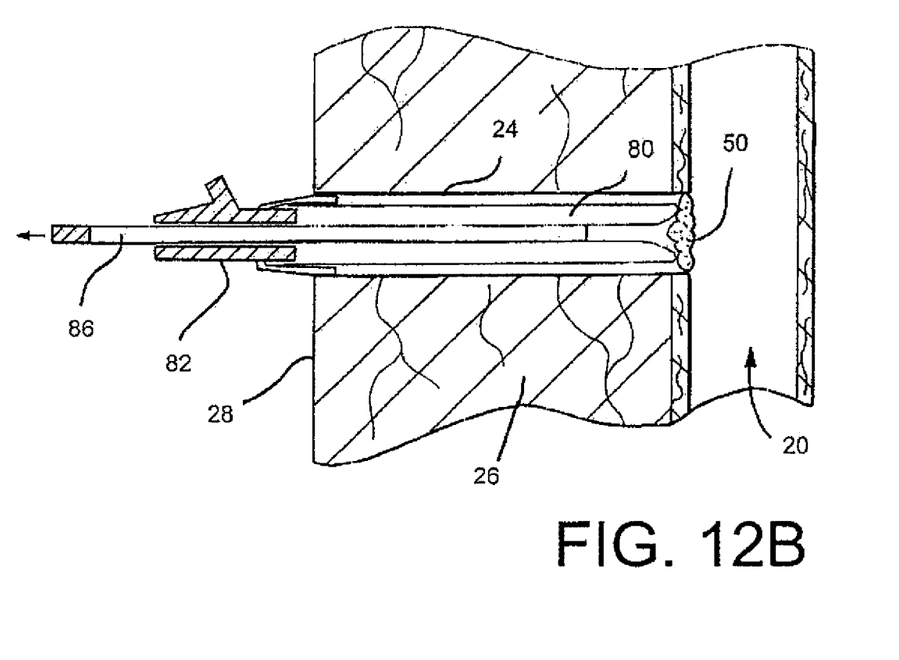
FIG. 12*b* is a sectional view of the alternative embodiment of FIG. 12*a* but depicted in a partially deployed configuration.
Figure 12C:
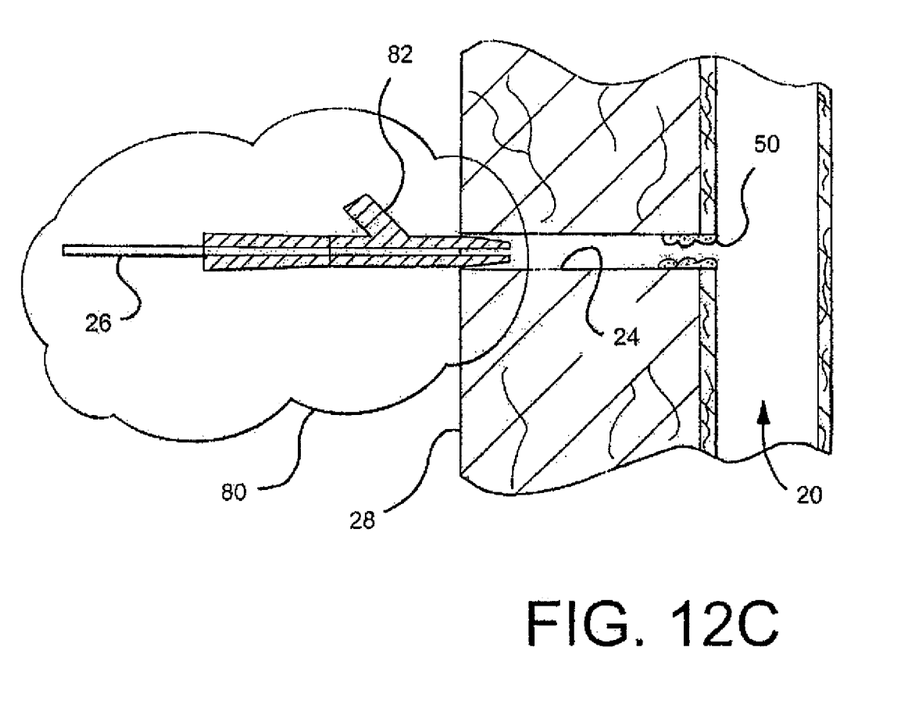
FIG. 12*c* is a sectional view of the alternative embodiment of FIG. 12*a* but depicted in a deployed configuration.

After the thrombus 50 fully forms in the tract 24 around the shaft 38, the balloon 40 can be deflated and fully withdrawn through a center opening 52 within the thrombus 50 as shown in FIG. 7. The working sheath 30 can be removed at the same time as well. A minimal amount of manual pressure or bandaging 53 can then be provided over the tract 24 to minimize blood loss until the opening 52 within the thrombus 50 fully closes as shown in FIG. 8. Using such a method, it has been determined that the closure of the opening 22 can be accomplished in less then five minutes at relatively low voltages and amperages, thus minimizing the discomfort to the patient as well. In addition, in order to lessen the likelihood of the thrombus being dislodged when the balloon 40 is retracted, a tank tread or rolling membrane balloon may be employed as depicted in FIGS. 12a-12c and described in further detail herein.

Referring again to FIGS. 5 and 6, it can be seen that more than one set of positive and negative electrodes are depicted. A first set of electrodes 44, 46 may be provided at proximal and distal ends of the balloon catheter 36, with a second set of electrodes 44a and 46a being provided on proximal and distal ends of the working sheath 30. Other combinations of one electrode on one element, and one electrode on another element ate possible as well. In addition, as the positive electrode is of importance in dictating the location of the resulting thrombus, if more than one thrombus is desired it is possible to position one positive electrode at a distal end of the balloon catheter or working sheath 30, and a second positive electrode at a position on the balloon catheter or working sheath closet to the negative electrode than the first positive electrode. Accordingly, a second thrombus (not shown) can be formed at an intermediate position within the middle of the tissue tract 24 for example as a secondary means of closure if it is desired In such an embodiment, it would be possible to only provide a single negative electrode with that one single negative electrode creating electric fields between it and both positive electrodes.

Figure 9:
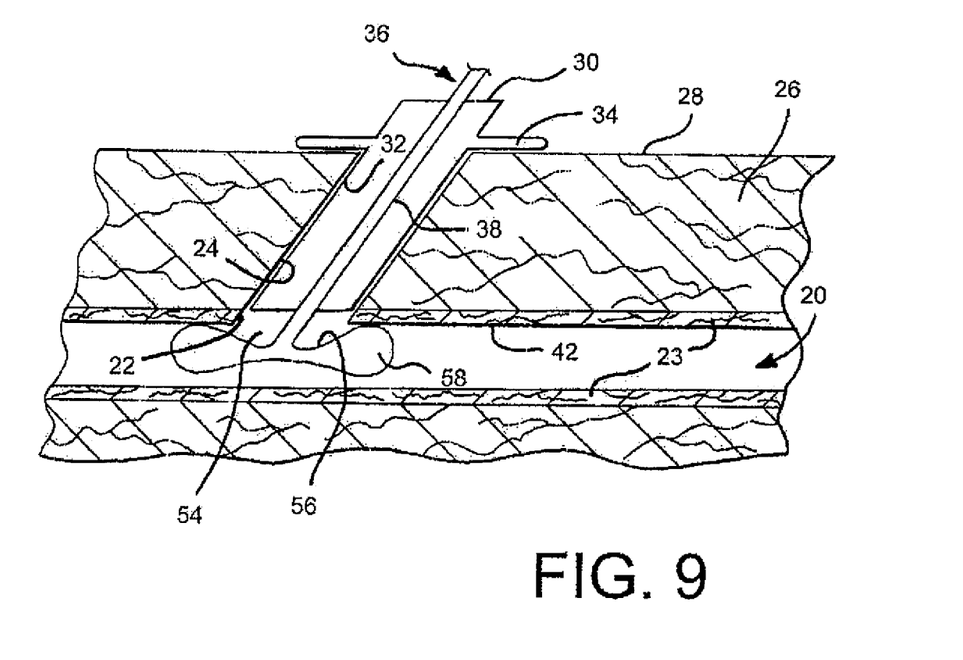
FIG. 9 is a sectional view of an alternative embodiment depicting a toroidal-shaped balloon.
Figure 10:
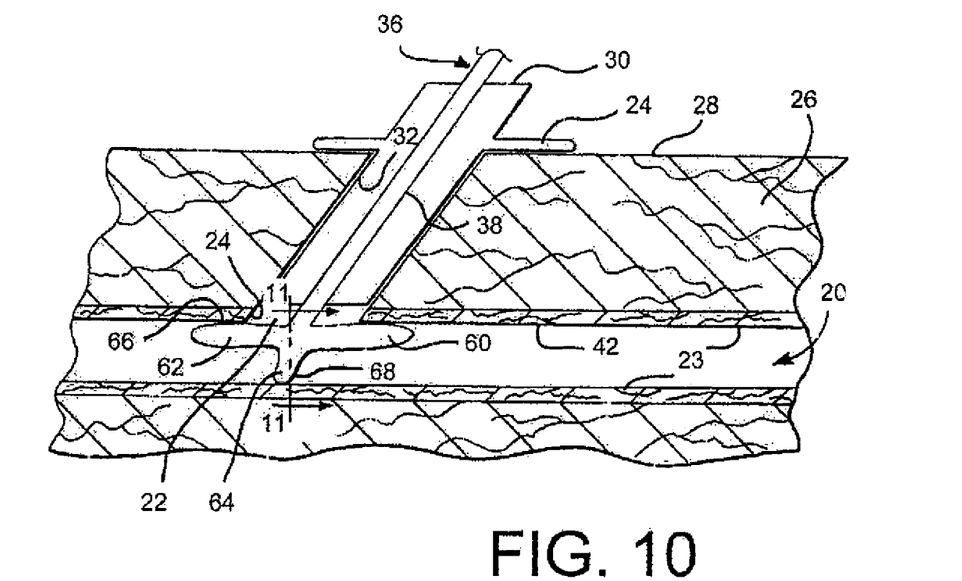
FIG. 10 is a sectional view similar to the previous views but depicting a self supporting balloon.
Figure 11:
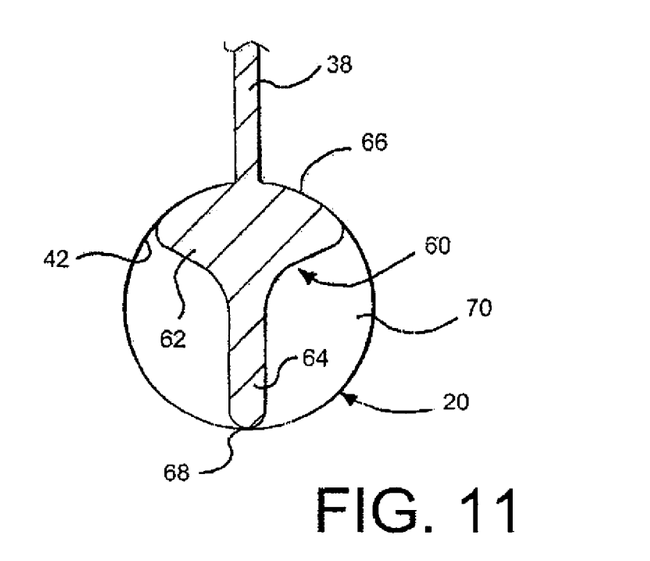
FIG. 11 is a sectional view of FIG. 10, taken along line 11-11 of FIG. 10, showing the self-supporting balloon extending across the blood vessel at two diametrically opposed points.

Referring now to FIGS. 9-11, alternative embodiments of the balloon are depicted. In order to facilitate the formation of the thrombus 50, the inventors have found that it is beneficial to create a pocket 54 between the upper surface 56 of a balloon 58 and the inner surface 42 of the blood vessel wall 20. The pocket 54 forms a natural recess into which the thrombus 50 can be formed when the electrodes are energized. In order to form the pocket 54 one version of the balloon 58 is provided in a toroidal shape in cross section.

In addition to the pocket 54, it may be beneficial to provide "self-supporting" balloon such as that depicted in FIGS. 10 and 11 As shown therein, the balloon 60 has a substantially T-shaped configuration in cross-section having an upper expanse 62 from which a leg 64 extends. The balloon 60, including its expanse 62 and leg 64 has a dimension so as to extend across the entire diameter of the blood vessel 20 and contact the inner surface 42 of the blood vessel 20 in at least two diametrically opposed locations denoted as points 66 and 68 in FIGS. 10 and 11. As also depicted in FIG. 11, it can also be seen that the T-shaped configuration of the balloon 60 does not substantially occlude the flow of blood through the blood vessel 20, but rather provides ample space 70 for such blood flow even when balloon 60 is inflated Such a "self-supporting" balloon provides significant strength as a backstop in that it engages the rear of the blood vessel, as well as the wall of the blood vessel proximate the opening Alternatively, the self-supporting balloon can be teardrop-shaped among other shapes.

Figure 13:
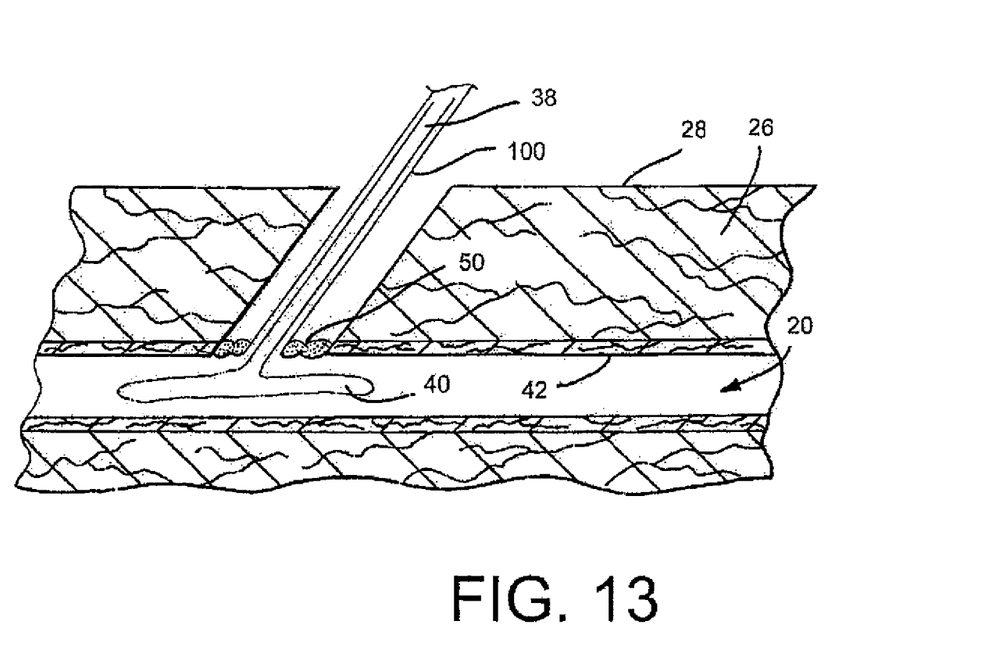
FIG. 13 is a sectional view of another alternative embodiment showing a removal sheath.
Figure 14:
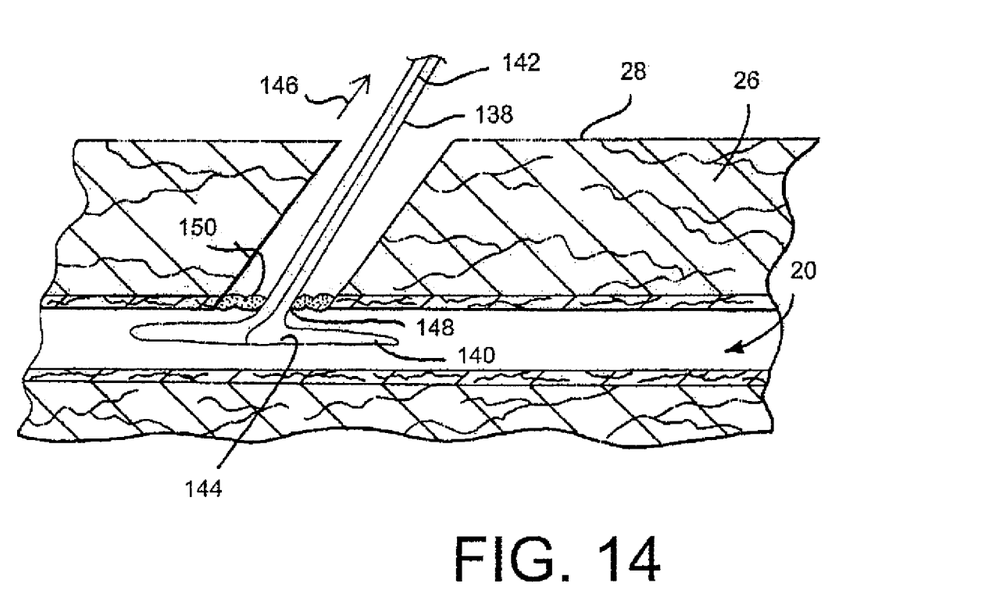
FIG. 14 is a sectional view of another alternative embodiment showing an everting balloon.
Figure 15:
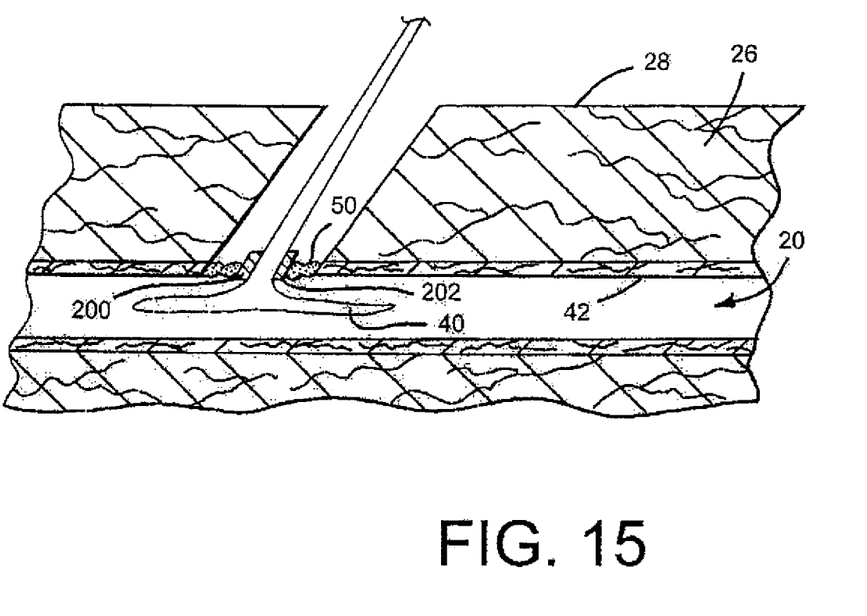
FIG. 15 is a sectional view showing another alternative embodiment including a sealing plug.

Referring now to the aforementioned FIGS. 12a-12c, a rolling membrane balloon 80 is depicted. The previously mentioned balloons can be thought of as "pre-formed" balloons having a balloon located at a distal end of a straight shaft. The balloon is inserted in a deflated condition, inflated, used as a backstop and locator while the thrombus is formed, deflated, and then retracted from the tissue tract. While effective, if it is desired to reduce the pulling force applied to the thrombus as the balloon catheter is retracted, and thus lessen the likelihood of the thrombus being dislodged thereby, the rolling membrane balloon can be used. With such a rolling membrane, the balloon 80 can be extended from a shortened, rolled-up configuration depicted in FIG. 12c to the configuration of FIG. 12b and ultimately to the configuration of FIG. 12a This extension and retraction can be achieved through the use of pressurized fluid and/or a mechanical rod. As shown in the figures, the balloon 80 may be connected to a manifold 82 and in turn to a pressurized fluid source 84 When the source 84 is in communication with the balloon 80, the balloon is caused to "roll-out" much like a tank tread from the position shown in FIG. 12c to that depicted in FIG. 12a. In turn when the balloon 80 is to return to the position shown in FIG. 12c, the balloon "rolls-up" thereby peeling away from the surface of the thrombus gradually, as opposed to simultaneously. This reduction in force may allow the thrombus to more likely remain in position. As shown, a push/pull or withdrawal rod 86 may be used to manually extend (roll-out) and retract (roll-up) the balloon 80 as opposed to relying solely on fluid pressure Two other approaches which can be used to facilitate removal of the balloon are depicted in FIGS. 13 and 14. In FIG. 13, a sheath 100 is placed in close proximity to the shaft 38 of the balloon so as to aid removing the balloon without disrupting the thrombus 50. In FIG. 14, an everting balloon 140 is shown The balloon 140 is similar to balloon 40 but for having a fiber or filament 142 extending through the shaft 138 and being connected to a bottom wall 144 of the balloon 140. Accordingly, when the filament 142 is pulled out of the patient in the direction of arrow 146, the balloon everts on itself, pulling away from within and peeling its outer surface 148 gradually away from the thrombus In any of the foregoing embodiments, the thrombus may be even more effectively formed by using a heat source in combination with the electrodes In such embodiments a resistive coil 88 or the like can be positioned at the distal end of one of the components of the apparatus, with coil 88 being shown as attached to the rod 86 in FIGS. 12a-12c as an example. The resulting rise in temperature of the blood and surrounding tissue facilitates coagulation as well Thrombus formation may also be aided by adding a biodegradable plug 200, such as collagen or fibrin, as shown in FIG. 15. The plug 200 could be positioned at a junction 202 of the subcutaneous tissue 26 and the blood vessel wall 42 In so doing, a surface for the thrombus 50 to attach to is provided The volume of material forming the plug 200 will reduce the time needed to create the thrombus mass adequate to ensure hemostasis and prevent hematoma.

With respect to the parameters of the electrical field generated by the electrodes, the inventors have found that the clot formation rate is dependent on a number of parameters including the type, intensity, duration, and other stimulation parameters of the electrode design. In addition, based on other requirements such as the time allotted for the thrombus to form, the size of the clot to form, the size of the wound to close, the contact impedance, etc, the electrical stimulation signal can be modified or chosen. For example, the electric field may be an alternating current, direct current, pulsed alternating current or pulsed direct current The intensity of the field can be adjusted based on amplitude, net energy, charged delivery, frequency, duty cycle, or other parameters. One particularly effective approach the inventors found was to use a DC positive signal continuously delivered to the thrombus site. The rate of clot formation increased with increased amplitude of the signal.

Based on the foregoing, it can be seen that the present disclosure provides an apparatus and method for effectively closing an opening in a blood vessel through the creation of an electric field in the area of the opening By appropriately positioning the positive electrode forming a portion of the electric field, blood cells are attracted to the positive electrode and a thrombus is quickly formed thereabout.

What is claimed is:

1. A method of closing an opening in a blood vessel, comprising:
    inserting a sheath into a tissue tract within a patient extending between an epidermis and a blood vessel wall;
    extending a balloon catheter into the sheath, the balloon catheter having a shaft terminating distally in a balloon, the balloon catheter being inserted until the balloon is fully within the blood vessel, one of the sheath or balloon catheter having a positive electrode thereon, one of the sheath and balloon catheter having a negative electrode thereon;
    inflating the balloon;
    retracting the balloon catheter until the inflated balloon engages an interior surface of the blood vessel wall; and
    creating an electric field between the negative and positive electrodes, blood cells thereby being attracted to the positive electrode and forming a thrombus at the blood vessel wall;
    wherein inflating and retracting the balloon causes a pocket to form between the balloon and the blood vessel wall.

2. The method of claim 1, wherein inflating the balloon causes the balloon to engage the blood vessel wall at least two diametrically opposed points.

3. The method of claim 1, wherein the balloon is self-supporting when inflated.

4. A method of closing an opening in a blood vessel, comprising:
    inserting a member between an epidermis of a patient and an opening of a blood vessel wall of the patient, the member having a positive electrode and negative electrode thereon;
    wherein the member is a working sheath;
    extending a balloon catheter through the working sheath until a balloon extending from a shaft of the balloon catheter is fully within the blood vessel, inflating the balloon, and retracting the balloon until it engages an interior surface of the blood vessel wall;
    forming a pocket between the balloon and the blood vessel wall to facilitate formation of a thrombus at the blood vessel wall; and
    then creating an electric field between the positive electrode and negative electrode, blood cells being attracted to the positive electrode and forming the thrombus at the blood vessel wall.

5. The method of claim 4, further includes inflating the balloon such that it engages at least two diametrically opposed points on the interior surface of the blood vessel wall.

6. The method of claim 4, further including heating a distal end of the member.

* * * * *